US007289837B2

(12) United States Patent
Mannheimer et al.

(10) Patent No.: US 7,289,837 B2
(45) Date of Patent: Oct. 30, 2007

(54) FOREHEAD SENSOR PLACEMENT

(75) Inventors: Paul D. Mannheimer, Danville, CA (US); Don Hannula, San Luis Obispo, CA (US); Donald E. Bebout, Lake Oswego, OR (US); Michael Patrick O'Neil, Sunnyvale, CA (US)

(73) Assignee: Nellcor Puritan Bennett Incorpoated, Pleasanton, CA (US)

( * ) Notice: Subject to any disclaimer, the term of this patent is extended or adjusted under 35 U.S.C. 154(b) by 550 days.

(21) Appl. No.: 10/678,040

(22) Filed: Oct. 1, 2003

(65) Prior Publication Data

US 2005/0070776 A1   Mar. 31, 2005

Related U.S. Application Data

(60) Provisional application No. 60/415,468, filed on Oct. 1, 2002.

(51) Int. Cl.
*A61B 5/00* (2006.01)
(52) U.S. Cl. ...................................................... 600/340
(58) Field of Classification Search ........ 600/309–310, 600/323, 340
See application file for complete search history.

(56) References Cited

U.S. PATENT DOCUMENTS

| | | | |
|---|---|---|---|
| 4,025,733 A | 5/1977 | Klar et al. | |
| 4,462,116 A | 7/1984 | Sanzone et al. | |
| 4,675,919 A | 6/1987 | Heine et al. | |
| 4,739,757 A | 4/1988 | Edwards | |
| 4,856,116 A | 8/1989 | Sullivan | |
| 4,977,011 A | 12/1990 | Smith | |
| 4,991,234 A | 2/1991 | Greenberg | |
| 5,826,277 A | 10/1998 | McConville | |
| 6,839,579 B1 * | 1/2005 | Chin | 600/323 |
| 2003/0236452 A1 * | 12/2003 | Melker et al. | 600/323 |

FOREIGN PATENT DOCUMENTS

| | | |
|---|---|---|
| DE | 29515877 U1 | 11/1995 |
| EP | 0631756 A1 | 1/1995 |

* cited by examiner

OTHER PUBLICATIONS

Bebout et al., "Effects of Cold-Induced Peripheral Vasoconstriction of Pulse Amplitude at Various Pulse Oximeter Sensor Sites" Published Abstract, Anesthesiology 2002; 96:A558.*

*Primary Examiner*—Eric F. Winakur
(74) *Attorney, Agent, or Firm*—Fletcher Yoder PC

(57) ABSTRACT

Forehead oximetry sensor devices and methods for determining physiological parameters using forehead oximetry sensors. One method includes placing an oximetry sensor on the forehead of a patient, such that the sensor is placed on the lower forehead region, above the eyebrow with the sensor optics placed lateral of the iris and proximal the temple; and operating the pulse oximeter to obtain the physiological parameter. In one aspect, the method also includes providing and placing a headband over the oximetry sensor, or alternately, the sensor is a headband-integrated sensor. The headband has an elastic segment sized to fit around the patient's head. The headband also includes a non-elastic segment that is smaller than and attached with the elastic segment. The non-elastic segment is sized to span a portion of the elastic segment when the elastic segment is stretched. In addition, the non-elastic segment is larger than the portion of the elastic segment it spans when the elastic segment is not stretched. When the headband or the headband-integrated sensor is sufficiently tight, it delivers a pressure in the range higher than the venous pressure and lower than the capillary pressure to the forehead of the patient.

8 Claims, 8 Drawing Sheets
(2 of 8 Drawing Sheet(s) Filed in Color)

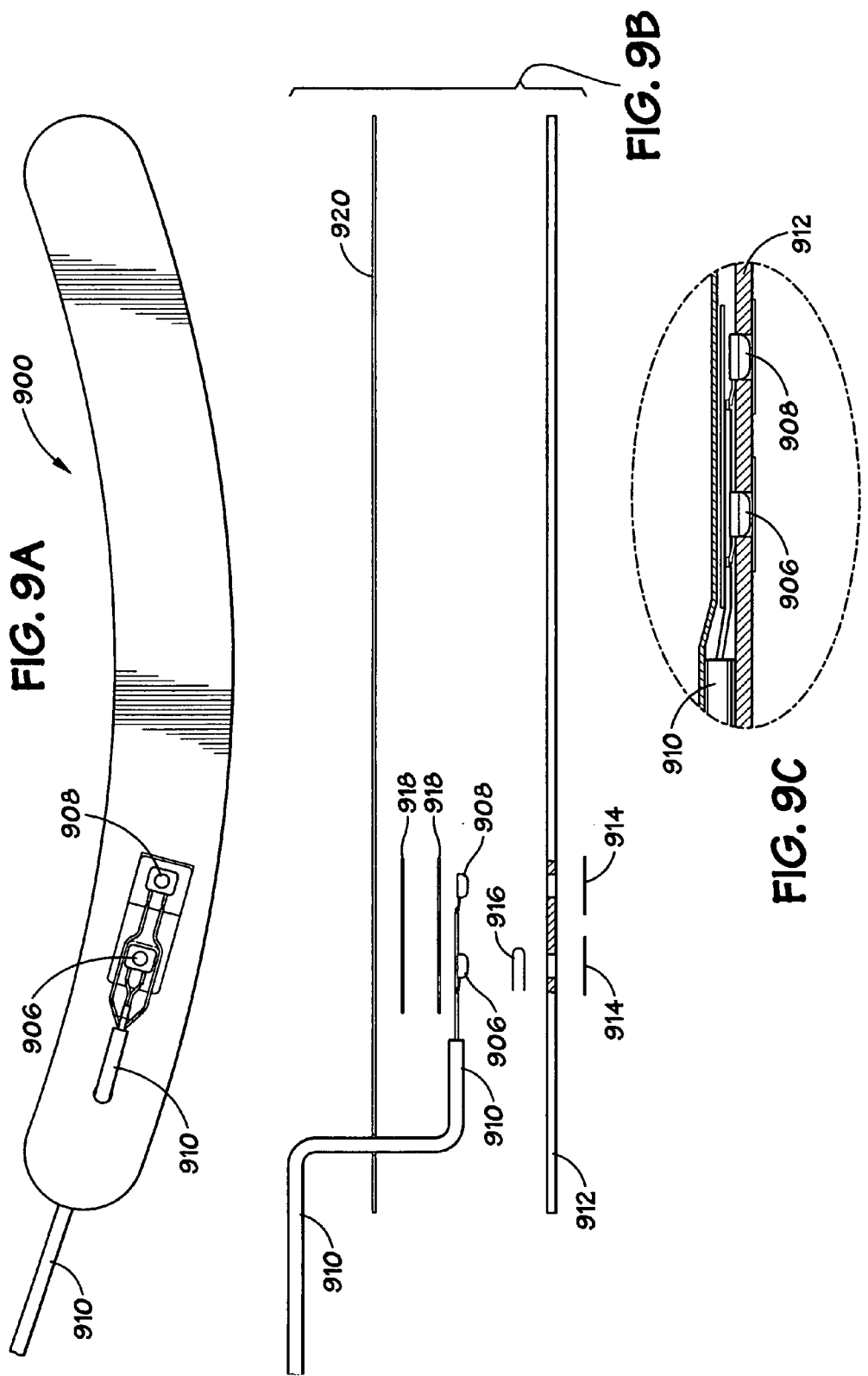

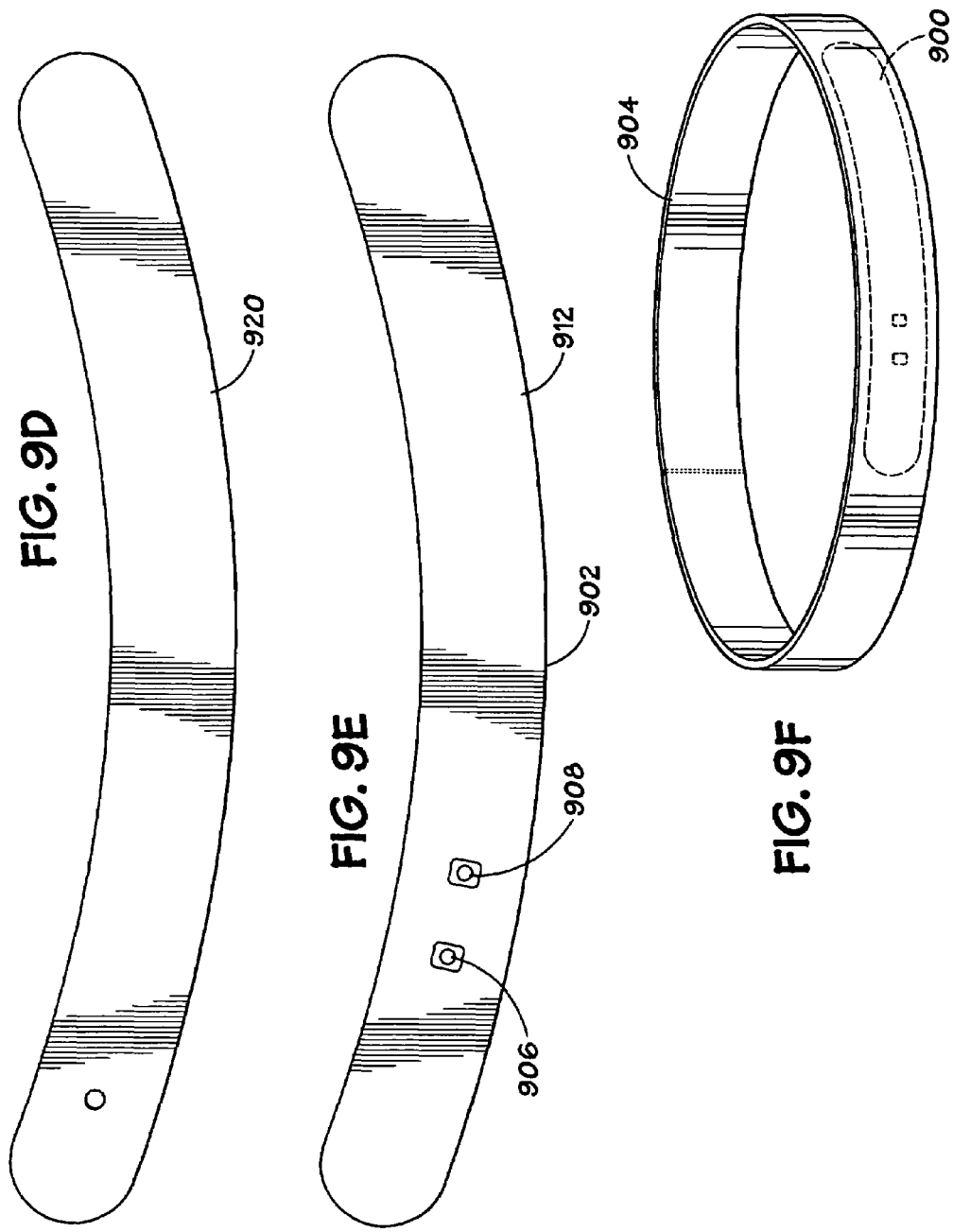

FOREHEAD SENSOR PLACEMENT

CROSS-REFERENCES TO RELATED APPLICATIONS

This application claims the benefit of U.S. Provisional Patent Application No. 60/415,468, filed Oct. 1, 2002, which application is incorporated herein by reference in its entirety for all purposes.

BACKGROUND OF THE INVENTION

The present invention relates to oximetry sensors and in particular to forehead-type oximetry sensors and methods of determining physiological parameters using forehead oximetry sensors.

It is known that the location on a patient's body where an oximetry sensor is applied can have an effect on the estimation of a physiological parameter that is determined using the sensor. It is also known that oximetry measurements can be obtained by placing an oximetry sensor on various locations on the body of a patient, including the fingertips, the earlobe, the foot, the head and so on. In order to have a proper sensor reading, there is a need for ensuring that the sensor is applied to an optimal location on a patient's body; a location where oximetry signals are stable and indicative of the actual physiological parameter which is being monitored.

BRIEF SUMMARY OF THE INVENTION

The present invention is directed towards forehead oximetry sensors and methods of determining physiological parameters using forehead oximetry sensors. In one embodiment, the present invention provides a method of determining a physiological parameter using a pulse oximeter. The method includes placing an oximetry sensor on the forehead of a patient, such that the sensor is placed on the lower forehead region, above the eyebrow with the sensor optics placed lateral of the iris and proximal the temple; and operating the pulse oximeter to obtain the physiological parameter. In one aspect, the method also includes providing and placing a headband over the oximetry sensor. The headband has an elastic segment sized to fit around the patient's head. The headband also includes a non-elastic segment that is smaller than and attached with the elastic segment. The non-elastic segment is sized to span a portion of the elastic segment when the elastic segment is stretched. In addition, the non-elastic segment is larger than the portion of the elastic segment it spans when the elastic segment is not stretched.

In another embodiment, the present invention provides a method for determining a location for the placement of an oximetry sensor. The method includes: measuring the temperature of a plurality of locations on an area of the body of a patient; dividing the temperature measurements into three categories including cold, warm and hot regions, wherein hot areas correspond with areas including those over large movable blood vessels and wherein cold areas correspond with areas including those susceptible to vasoconstriction; and selecting the area that is not hot and not cold as a location for the placement of the sensor.

In another embodiment, the present invention provides a method for determining a location for the placement of an oximetry sensor. The method includes: providing a pulse oximeter having a monitor and a sensor; placing the sensor on a location on the body of a patient; measuring a pulse amplitude using the sensor; comparing the pulse amplitude to a threshold; and recommending a new sensor location using the monitor if the pulse amplitude is lower than the threshold.

In another embodiment, the present invention provides an oximeter sensor, having a substrate having a shape similar to a shape of at least a portion of a patient's forehead and including a section adapted to substantially fit over a portion of a forehead of a patient. The sensor includes an emitter disposed on the substrate at a position located on the section and a detector disposed on the substrate at a distance from the emitter; and a headband for holding the substrate against the patient's forehead, where the headband is sized to fit around the patient's head. In one aspect, the headband includes an elastic segment sized to fit around a patient's head; and a non-elastic segment that is smaller than and attached with the elastic segment. The non-elastic segment is sized to span a portion of the elastic segment when the elastic segment is stretched, and the non-elastic segment is larger than the portion of the elastic segment it spans when the elastic segment is not stretched. In another aspect, the headband's non-elastic segment is sized to not project out from the surface of the elastic portion when the headband is sufficiently tight, thus indicating an adequate level of tension corresponding with delivering a pressure in the range higher than the venous pressure and lower than the capillary pressure to the forehead of the patient.

For a further understanding of the nature and advantages of the invention, reference should be made to the following description taken in conjunction with the accompanying drawings.

BRIEF DESCRIPTION OF THE DRAWINGS

The patent or application file contains at least one drawing executed in color. Copies of this patent or patent application with color drawing(s) will be provided by the Office upon request and payment of the necessary fee.

FIG. 9 is an assembly drawing of an embodiment of a headband-integrated sensor.

DETAILED DESCRIPTION OF THE INVENTION

Figure 1:
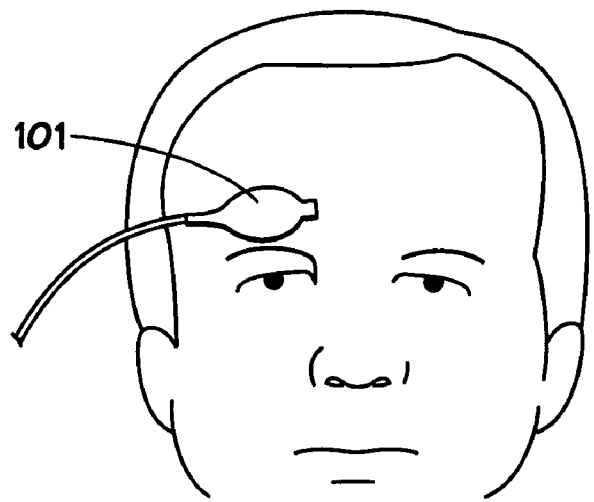
FIG. 1 is a diagram of a forehead oximetry sensor applied to a patient.

The embodiments of the present invention are directed towards forehead oximetry sensors and methods of determining physiological parameters using forehead oximetry sensors. During oximetry, a forehead oximetry sensor 101 (e.g., such as those manufactured by Nellcor Puritan Bennett, the assignee herein), is placed on a patient's forehead, as is shown in FIG. 1. A typical pulse oximeter measures two physiological parameters, percent oxygen saturation of arterial blood hemoglobin ($SpO_2$ or sat) and pulse rate. Oxygen saturation can be estimated using various techniques. In one common technique, the photocurrent generated by the photo-detector is conditioned and processed to determine the ratio of modulation ratios (ratio of ratios) of the red to infrared signals. This modulation ratio has been observed to correlate well to arterial oxygen saturation. The pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING", issued Dec. 29, 1998, and U.S. Pat. No. 4,911,167, entitled "METHOD AND APPARATUS FOR DETECTING OPTICAL PULSES", issued Mar. 27, 1990, and the relationship between oxygen saturation and modulation ratio is further described in U.S. Pat. No. 5,645,059, entitled "MEDICAL SENSOR WITH MODULATED ENCODING SCHEME," issued Jul. 8, 1997, the disclosures of which are herein incorporated by reference in their entirety. Most pulse oximeters extract the plethysmographic signal having first determined saturation or pulse rate.

Figure 2:
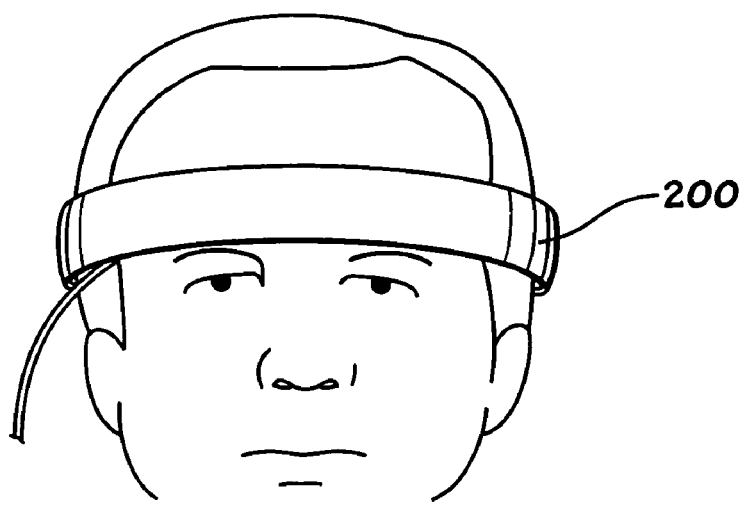
FIG. 2 is a diagram of a forehead oximetry sensor held to a patient's forehead with a headband.

The force applied to the forehead oximetry sensor can be a factor in the proper functioning of the sensor. Generally, a headband is not required to be worn with a forehead oximetry sensor, when the patient's head is upright and/or well above the chest, and/or when the patient has normal venous pressure. In certain clinical scenarios, a headband 200 is required to be used in conjunction with a forehead sensor 101 (e.g., an oximetry sensor), as is shown in FIG. 2. FIG. 2 shows the sensor leads extending from the sensor (not shown) outward from beneath the headband. Such clinical scenarios include scenarios where: patient is lying down with his/her head near or below chest level; patient is subject to elevated venous pressure; patient is diaphoretic; patient is moving excessively, such as during exercise; as well as other scenarios where venous pulsations can introduce errors in oximetry calculations. In those scenarios, without a headband, or force on the oximetry sensor, venous pulsations could cause an incorrect interpretation of the waveform, and therefore result in a less than accurate determination of the oxygen saturation and pulse rate values. The headband can be used to apply pressure to the oximetry sensor, thus reducing the effects of venous pulsations. When used to support an oximetry sensor, the amount of force applied by the sensor on the forehead should be greater than the venous pressure, but less than the arteriole pressure. Generally, a good pressure range is one where the applied pressure is higher than venous pressure (e.g., 3–5 mm Hg) and lower than the capillary pressure (e.g., 22 mm Hg). Preferably, this should be between 15 mm Hg and 20 mm Hg in the adult patient. Exemplary headbands having a pressure or tension indicator are described in a co-pending U.S. patent application Ser. No. 10/779331, entitled: "Headband with Tension Indicator," the disclosure of which is herein incorporated by reference in its entirety for all purposes. As set forth in that co-pending patent application, the headband may be adjusted for use with any size wearer by using an adjustable closure mechanism, such as for example a hook and loop closure mechanism. The user can apply a wide range of pressures to the forehead oximetry sensor depending on the amount of tension which has been applied to the headband during its placement around the wearer's head. In addition, the tension or pressure indicating headband disclosed therein, may be used to help establish an acceptable window of pressure for the sensor's attachment with a patient. The headband when used with a forehead oximetry sensor assists in holding the sensor in place and applies a gentle pressure to expel any pulsating venous blood.

The inventors having conducted various physiological studies have determined that in addition to the possibility of needing to apply an oximetry sensor to the forehead of a patient with a certain amount of pressure, the actual location where the forehead oximetry sensor is applied is also a contributor to the ultimate estimation of physiological parameters determined using the forehead oximeter. An exemplary forehead oximetry sensor is described in a co-pending U.S. patent application Ser. No. 10/256,245, entitled: "Stacked Adhesive Optical Sensor," the disclosure of which is herein incorporated by reference in its entirety for all purposes.

The physiological studies conducted by the inventors herein have not only lead to the discovery of preferred locations for the placement of a forehead oximetry sensor, but have also discovered why the forehead and in particular the lower forehead is a preferred sensor location.

Figure 3A:
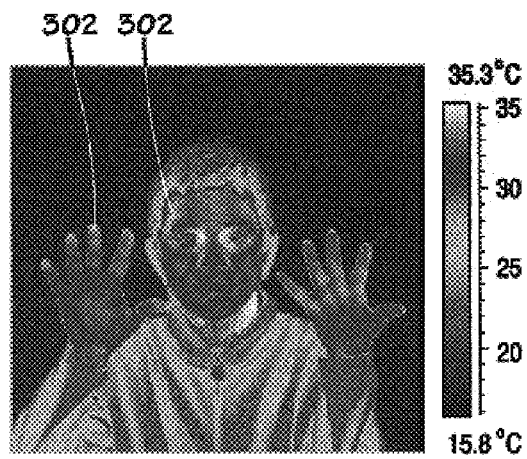
FIGS. 3A–C are thermal images of a person's hands and head in a warm room and after cold room exposure for approximately 45 minutes.
Figure 3B:
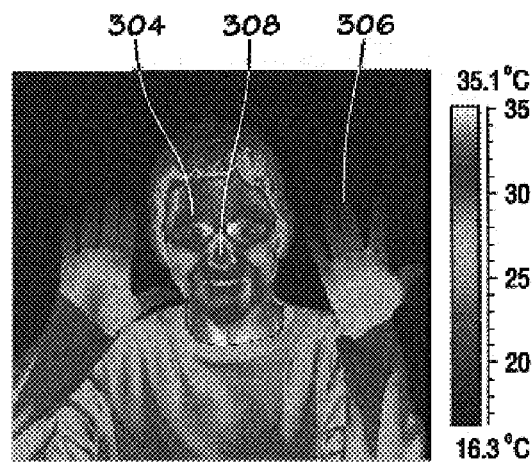
Figure 3C:
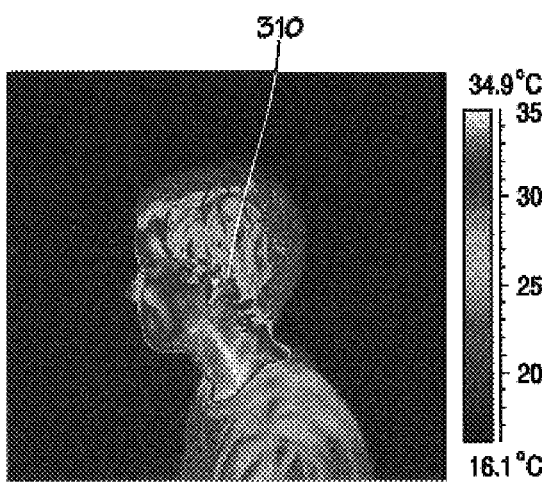

FIGS. 3A–C are thermal images of a person's hands and head in a warm room and after cold room exposure for approximately 45 minutes. These thermal images show warm and cool regions of the head and hands in warm and cold room environments. A cold room environment corresponds with the environment of some operating rooms, whereas a warm room corresponds to other locations. FIG. 3A shows a thermal image of a person's head and hands when the person is located in a room maintained at approximately 72° F. (22° C.) (warm room). As can be seen from this figure, regions 302, which include the head, the fingers and the ears are warm skin regions, indicating regions where there is adequate blood perfusion and hence regions where good oximetry readings can be obtained. In contrast, FIGS. 3B–C show thermal images of the same person as in FIG. 3A, after she has been exposed to a cold room maintained at approximately 58° F. (14.4° C.) for approximately 45 minutes. These figures (FIGS. 3B–C) show that after the exposure to the cold room, region 304, (the head) is the only warm region, whereas the fingers 306, the nose 308 and the ears 310 are cold, indicating regions where there is inadequate blood perfusion and hence regions where poor pulse reading are expected to occur.

Figure 4:
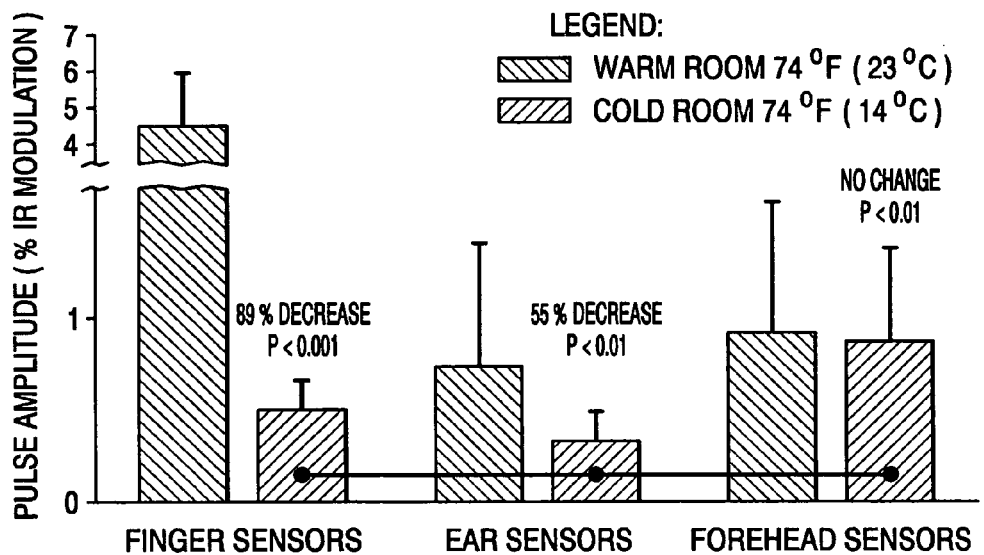
FIG. 4 is a graph showing pulse amplitude signal variations due to a change in the environment's temperature obtained from various sensors located at various locations on a patient's body.

FIG. 4 is a graph showing pulse amplitude signal variations due to a change in the environment's temperature obtained from various sensors located at various locations on a patient's body. This figure shows pulse amplitudes (e.g., % IR [infrared] modulations) obtained using finger, ear, and forehead sensors for humans in a warm room and a cold room. Shown in this figure are the changes in pulse amplitude caused by cold-induced vasoconstriction. As can be seen, the forehead is not significantly affected, while ear and fingers show a strong vasoconstrictive response, because the pulse amplitude obtained by the forehead sensor shows no significant change as the patient is moved from a warm to a cold room. The results of this graph indicate that the lower-forehead region where the forehead sensors were applied provides the most stable pulsatile signal strength of the three sites during vasoconstriction. Other results indicate that the head provides an earlier indication of changes in $SaO_2$ than other sites due to a phenomenon known as circulation delay. This phenomenon provides that hands or fingers, especially in a cold room (e.g., operating room in a surgical unit) see changes in core arterial oxygen saturation events up to a minute later than when it occurs. Clearly such delays can adversely impact a patient's condition.

Figure 5:
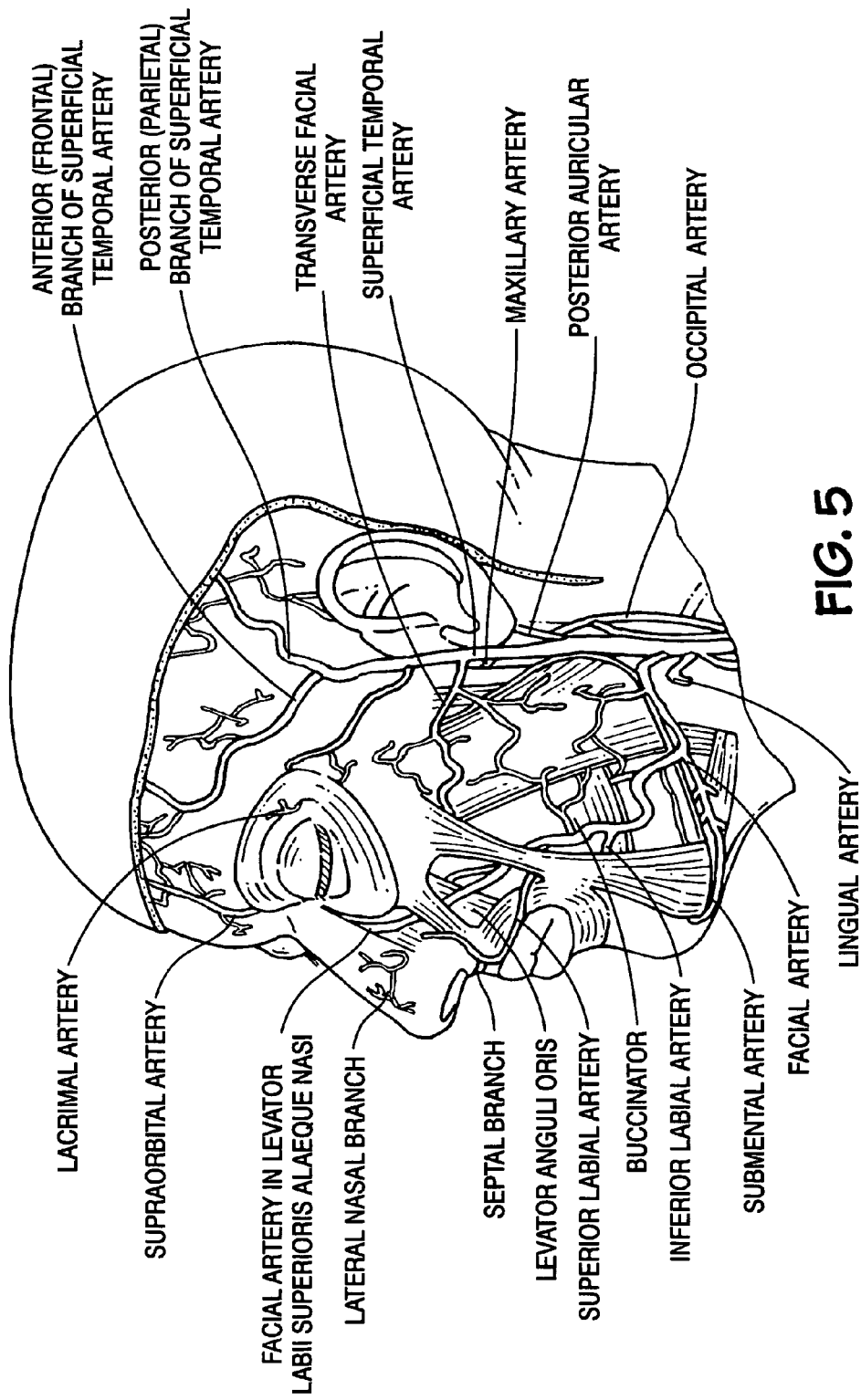
FIG. 5 is a diagram of the arteries in a human head.
Figure 6:
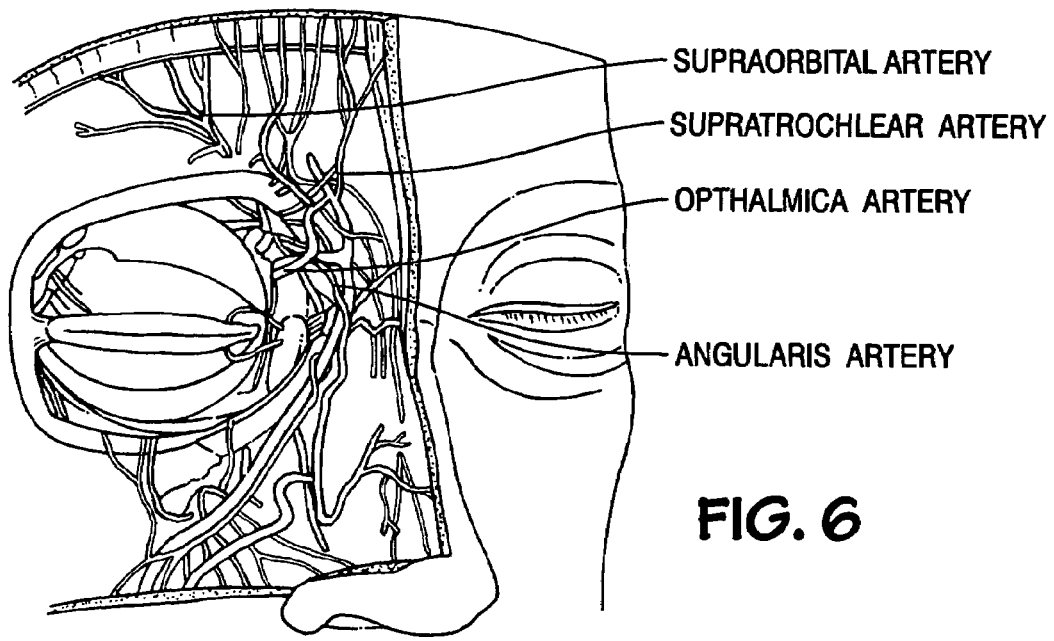
FIG. 6 is a detailed diagram of the arteries around a human eye.

A reason for this vasoconstrictive effect is understood by examining the arteries of the head region, as shown in FIG. 5. This figure shows that the external carotid artery feeds most of the head skin including the ears. The lower-forehead skin is fed by the supraorbital artery, which arises from the internal carotid artery. The external carotid artery does not supply the brain, and the circulation it supports shows more vasoactivity and vasoconstrictor reflexes that the circulation of the lower-forehead region. Referring to FIG. 6, it is shown that the same internal carotid artery source that supplies blood to the eyes and brain supplies the skin directly above the eyebrows. The external carotid artery supplies other facial tissues. Vasoconstrictive response affects the internal branch of the carotid artery less than the external branch of the carotid artery. Therefore, since the lower-forehead blood flow stems from the same circulation that feeds the brain, it is less affected by vasoconstriction, and hence is a more stable and predictable location for oximetry sensor placement.

Figure 7:
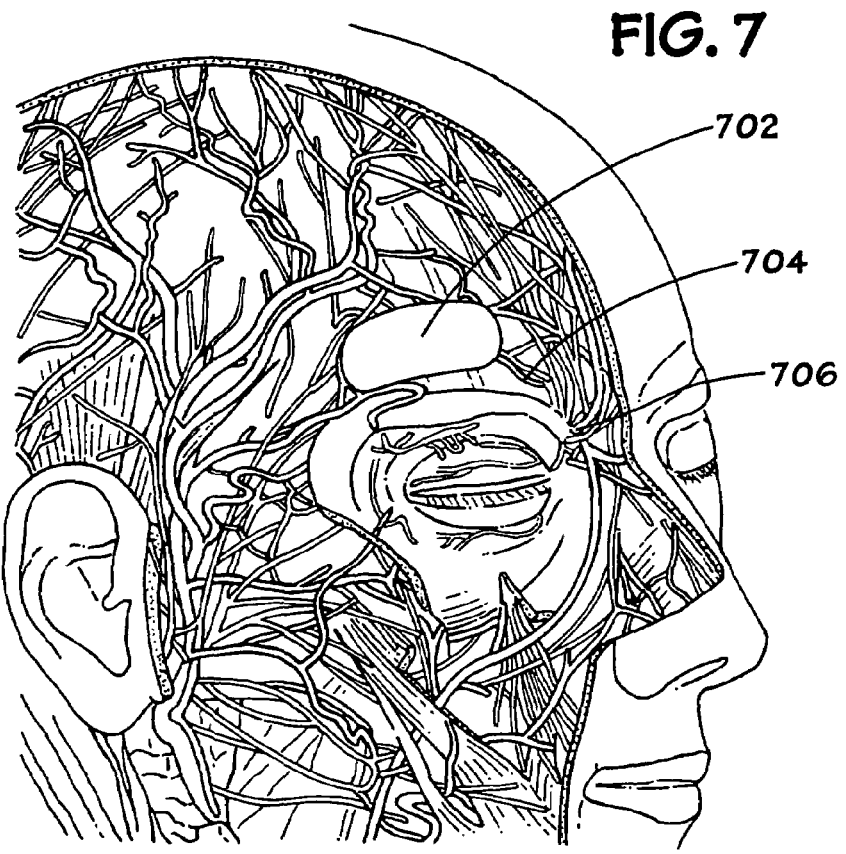
FIG. 7 is a diagram of the arteries in a human head and a preferred location for an oximetry sensor.

Having identified and understood why that the lower forehead region is a preferred location for placing an oximeter sensor, a preferred location on the lower forehead is next described. A preferred sensor placement enables a sensor to optically probe arterial circulation that is fed by the internal carotid artery. In addition, such a preferably-placed sensor probes richly perfused regions of the microvasculature, with little interference from larger blood vessels; and also probes cardiac-induced pulsating arterial blood, with little interference from venous pulsations. FIG. 7 shows such a sensor location to be the lower forehead region 702, immediately above the eyebrow 704, with both the sensor optics (i.e., emitter and detector) located lateral of the iris 706 and proximal the temple. Alternately, the preferred sensor placement is one where the sensor's emitter and the detector are directly above the eyebrow, such that the emitter and detector are both located lateral of the supratroclear and supraoclear arteries and medial the superficial temporal artery, or in other words, placing the emitter or detector directly above the center of the eye close to the eyebrow, and the other (detector or emitter) approximately horizontally located towards the sides of the head, a few millimeters away (e.g., 2–3 mm to 15 mm). Preferably, the sensor emitter or detector is placed within ±5 mm of the vertical line passing through the location of the iris, more preferably 0 mm–3 mm lateral the iris, and the other of the emitter and detector is placed horizontally lateral this location. Preferably also, the axis connecting the sensor optics is placed within 10 mm of the top of the eyebrow, and more preferably within 5 mm. This placement site is preferred because it experiences little vasoconstriction since the circulation in this region is fed by the internal carotid artery. In addition, this region is preferred because it experiences strong pulsatile signals, with little interference from large blood vessels.

A review of FIG. 7 also shows locations that are less preferred locations for the placement of a forehead sensor. For example, the region of the upper or center of forehead, scalp and facial regions are less preferred region for sensor placement, because this region has superficial vasoactive vessels perfused with blood from external carotid circulation. In addition, sites over large blood vessels, such as the temporal artery are also a lesser-preferred location for sensor placement. For sites over the large blood vessels, the $SpO_2$ readings become unreliable when the sensor light probes large light-absorbing objects that move or change diameter with the heartbeat, where both red and infrared light signals become similarly modulated by the highly opaque vessels, unrelated to the oxygen saturation of arterial blood. Regions over large pulsing blood vessels, such as the temporal and proximal regions of the supraorbital arteries themselves, should preferably not be used as sensor placement sites.

Figure 8:
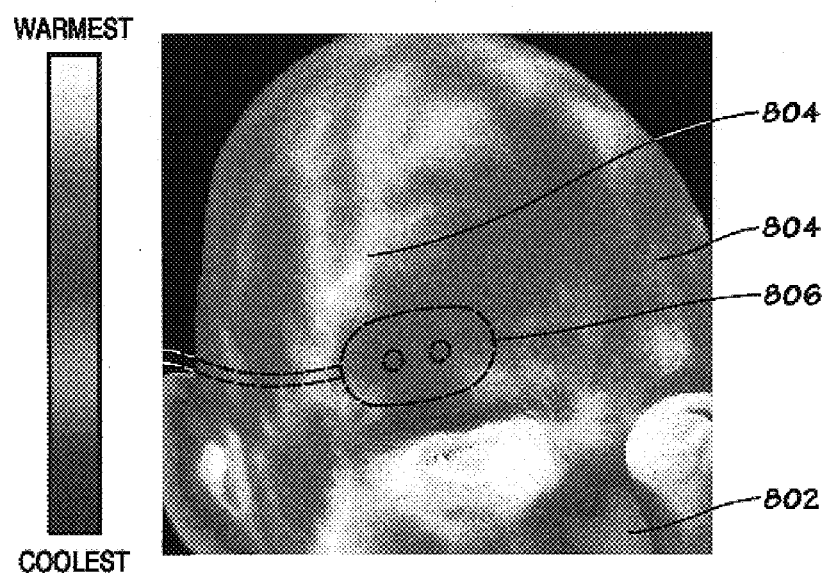
FIG. 8 is an infrared thermal image of a human head illustrating a proper sensor placement.

FIG. 8 shows an infrared thermal image of a human head illustrating a proper sensor placement. This figure shows the cooler region 802 in and around the nose to be a less preferred location for sensor placement, because the tissue in this region has smaller pulses, and because the region is subject to vasoconstriction. This figure also shows that region 804 being the warmest region is also a lesser preferred region for sensor placement, because the regions directly above larger vessels (hence warmer) are subject to cardio-synchronous vessel movement. In region 804, while the pulsatile signal strength may seem desirable, $SpO_2$ readings could be unreliable. In contrast, region 806, which is above and lateral the center of either eyebrow, is a preferred sensor placement location. As is shown in the figure, a preferred placement for a forehead sensor, such the sensor described in co-pending U.S. patent application Ser. No. 10/256,245, entitled: "Stacked Adhesive Optical Sensor," is to place the emitter above and slightly lateral the iris, with the sensor cable routed back towards the ear. Accordingly, a method for determining a location for the placement of an oximetry sensor, includes: measuring the temperature of a plurality of locations on an area of the body of a patient; dividing the temperature measurements into three categories, namely cold, warm and hot regions; rejecting the hot areas corresponding to areas over large movable blood vessels as a location for the placement of the sensor; rejecting the cold areas corresponding to areas susceptible to vasoconstriction as a location for the placement of the sensor; and selecting the area that is not hot and not cold as a location for the placement of the sensor. The temperature measurement apparatus can be a thermal strip that is made part of the sensor. Alternately, the temperature measurement apparatus may be a part of a sensor attachment device, such as a headband or a hat. Yet alternately, the temperature measurement apparatus may be a separate temperature measurement device packaged with the sensor or the attachment device. Another method for identifying regions over larger cardio-synchronously moving vessels is to palpate the skin; regions in which pulses can be felt to the touch should be avoided, while regions with no or minimal pulsations present represent preferred locations for sensor placement.

In light of the disclosures directed to determining a proper sensor placement location, the sensor's mechanical design itself can be configured for efficient locating on the forehead and above the eye. Such a design has a sensor height (or width) that is smaller than its length. For example, a sensor with a height (or width) smaller than 5 millimeters and length between 6–15 mm satisfies such a configuration. The remaining details of such a sensor are disclosed in the above-referenced and co-pending U.S. patent application Ser. No. 10/256,245, entitled: "Stacked Adhesive Optical Sensor".

As set forth above, an attachment device is described in a co-pending U.S. patent application Ser. No. 10/779,331 entitled: "Headband with Tension Indicator." So, in addition to above disclosures directed to the placements of an oximetry sensor, such placements may include the positioning of a headband device over the sensor to hold the sensor in place on the patient's forehead and also to provide a gentle pressure to the forehead sensor.

Alternately, the forehead sensor can be integrated with a sensor attachment device, such as a headband. FIG. 9 is an assembly drawing of an embodiment of a headband-integrated sensor. A headband-integrated sensor provides for a more secure and stable placement of a sensor on a patient's forehead than that of two-piece device having a separate sensor and a headband, especially for patient's who move excessively, such as neonate patients. For such patients it is much easier to apply one integrated sensor, as opposed to applying a sensor and then a separate headband over the sensor. FIG. 9 shows an oximeter sensor placed on a substrate 902 that can be placed, adhered, or integrated into a headband 904. In the headband-integrated embodiment, the sensor uses an emitter 906 containing two discrete wavelengths and a detector 908 placed more than 2 mm away, and ideally 10 mm–15 mm from the emitter. The surface 902 can be black in order to minimize any shunting of light between sensor and patient skin. The sensor in a headband could be used in conjunction with a small, portable oximeter to allow mobility of the user during activities. Also shown in FIG. 9 is a cable 910 for providing drive current to the LED and for providing the detector signal to the oximeter. The cable provides the electrical connection to the monitor; it also provides power for the emitter, signal carrying conductors from the detector, and shielding to protect the small signals from the detector against external electrical interference.

The sensor is shown in a multi-layer structure having a face portion 912. The face 912 is the surface that is placed against the patient's skin. The face material may have an adhesive layer such as an acrylic or synthetic rubber adhesive, or it may be without adhesive, and typically made from a foam PVC or foam polyurethane material. The face 912 component is preferably black so as to minimize the incidence of reflected light that does not go through the tissue. Below the face layer 912 are two windows 914. The windows 914 are generally a clear component, such as for example, a thin film or a clear molded plastic component that makes contact with the skin. The thin film window may be a polyurethane or an acrylic adhesive on a polyester film. The intent of the window 914 is to provide an efficient optical coupling mechanism between the optical components (emitter and detector) and the skin. Located above the face 914, is a Faraday shield 916. The Faraday shield 916 is a conductive material, for example, a copper film or copper mesh, that is electrically connected to the monitor ground to help shield the detector from extraneous electrical interference while passing light to the detector. Next located are the LED 906 and the detector 908. Above the LED and the detector is a mask layer, which may include more than one mask layer. The mask layer 918 is generally a thin film that is intended to block light from entering the back side of the sensor, or from traveling directly from emitter to detector (shunt light). The purpose of the mask 918 is to ensure that all of the light reaching the detector is light from the emitter that has traveled through the capillary bed. Above the mask layer 918 is the back layer 920. The back or the top layer is the non-tissue contacting surface of the sensor. This layer may include a cosmetic finish for the sensor, which can be white with some printed artwork identifying the sensor. Typical materials may be Velcro loop, or soft PVC foam.

Figure 10:
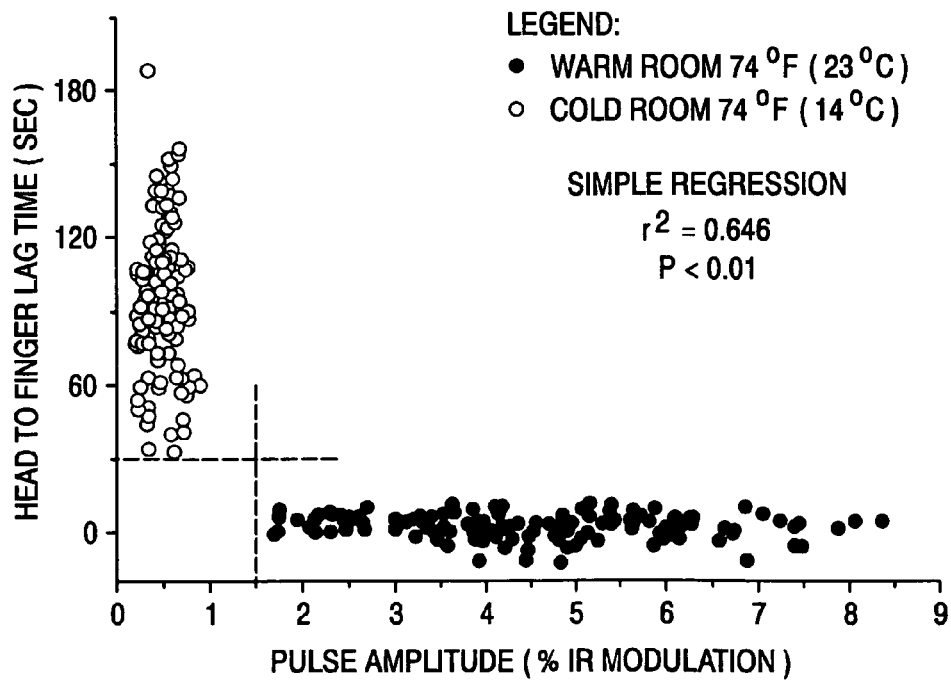
FIG. 10 is a graph of the relationship between Lag Time and Pulse Amplitude.

FIG. 10 is a graph of the relationship between Lag Time in detecting a change in oxygenation status of a patient and Pulse Amplitude. FIG. 10 shows the head to finger time delay in seconds vs. pulse amplitude in % infrared (IR) modulation for values taken in a warm room as well as those taken in a cold room as observed in healthy volunteers. This figure shows a clear clustering of the data points, where the data points taken in a cold room and hence indicative of vasoconstriction all show small pulse amplitude values (e.g., less than 1.5%) and longer head to finger lag times. On the other hand, the data points corresponding to values not impacted by vasoconstriction (warm room data) show a small time lag and larger pulses. Accordingly, a method for determining a location for the placement of an oximetry sensor includes: measuring pulse modulation value, comparing the modulation value to a threshold, and recommending a new sensor location to be chosen by the caregiver. This recommendation has particular value when the initial sensor placement is peripherally located, such as on a finger. The recommendation may be made by the monitor coupled with the sensor using an algorithm being executed by the monitor and communicated to a caregiver using the monitor's audible or visual indicators.

As will be understood by those skilled in the art, the present invention may be embodied in other specific forms without departing from the essential characteristics thereof. These other embodiments are intended to be included within the scope of the present invention, which is set forth in the following claims.

What is claimed is:

1. A method for determining a location for the placement of an oximetry sensor, comprising:
measuring the temperature of a plurality of locations on an area of the body of a patient;
dividing the temperature measurements into three categories comprising cold, warm and hot regions,
wherein hot regions correspond with areas including those over large movable blood vessels and
wherein cold regions correspond with areas including those susceptible to vasoconstriction; and
selecting the region that is not hot and not cold as a location for the placement of the sensor.

2. The method of claim 1 wherein the region that is not hot and not cold corresponds to the lower forehead of the patient.

3. The method of claim 1 wherein the region that is not hot and not cold is substantially absent superficial vasoactive vessels perfused with blood from external carotid circulation.

4. The method of claim 1 wherein the hot regions correspond to the upper and middle forehead of the patient.

5. The method of claim 1 wherein the cold regions correspond to the hands of the patient.

6. The method of claim 1 wherein the cold regions correspond to the fingers of the patient.

7. The method of claim 1 wherein the cold regions correspond to the nose of the patient.

8. The method of claim 1 wherein the cold regions correspond to the ears of the patient.

* * * * *